US00PP33484P2

(12) United States Plant Patent
Verschoor

(10) Patent No.: US PP33,484 P2
(45) Date of Patent: Sep. 14, 2021

(54) ***ACHILLEA* PLANT NAMED 'VERSDIDEM'**

(50) Latin Name: *Achillea ptarmica*
Varietal Denomination: Versdidem

(71) Applicant: Janus Verschoor, Haarlem (NL)

(72) Inventor: Janus Verschoor, Haarlem (NL)

(73) Assignee: A. Verschoor Horticulture import-export B.V., Haarlem (NL)

( * ) Notice: Subject to any disclaimer, the term of this patent is extended or adjusted under 35 U.S.C. 154(b) by 0 days.

(21) Appl. No.: 17/104,297

(22) Filed: Nov. 25, 2020

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Achillea ptarmica* plant named 'Versdidem' that is characterized by its very floriferous flowering habit, its ray florets that are snowy white in color on pompom shaped inflorescences, its good resistance to powdery mildew, its foliage that is medium green in color and fine-toothed margins, its compact, rounded and dense plant habit, and its efficient unrooted cutting production.

2 Drawing Sheets

Botanical classification: *Achillea ptarmica.*
Variety denomination: 'Versdidem'.

CROSS REFERENCE TO A RELATED APPLICATION

This application is related to a European plant breeders' rights application filed on Jun. 16, 2018, application No. 2018/1532. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Achillea ptarmica* named 'Versdidem', and is hereinafter referred to by its cultivar name 'Versdidem'. 'Versdidem' is a new cultivar of Siberian statice, a hardy perennial grown for landscape use.

The new cultivar was discovered as a chance seedling in a trial field by the Inventor in Haarlem, The Netherlands in 2016. The trial field contained thousands of plants of *Achillea ptarmica* proprietary seedlings and cultivars. The parentage of 'Versdidem' is therefore unknown.

Asexual propagation of the new cultivar was first accomplished under the direction of the Inventor by stem cuttings in 2016 in Haarlem, The Netherlands. Asexual propagation of the new cultivar by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Versdidem' as a new and unique cultivar of *Achillea.*

1. 'Versdidem' exhibits a very floriferous flowering habit.
2. 'Versdidem' exhibits ray florets that are snowy white in color on pompom shaped inflorescences.
3. 'Versdidem' exhibits good resistance to powdery mildew.
4. 'Versdidem' exhibits foliage that is medium green in color and fine-toothed margins.
5. 'Versdidem' exhibits a compact, rounded and dense plant habit.
6. 'Versdidem' exhibits efficient unrooted cutting production.

'Versdidem' can be most closely compared to the *Achillea* cultivars 'Perry's White' (not patented), 'The Pearl' (not patented), and 'Peter Cottontail' (U.S. Plant Pat. No. 31,756). All are similar to 'Versdidem' in having inflorescences that are white in color. 'Perry's White' differs from 'Versdidem' in having a much taller plant height and flowers that are smaller in size. 'The Pearl' differs from 'Versdidem' in having a taller plant height. 'Peter Cottontail' differs from 'Versdidem' in having a much taller plant height and in having an upright and cylindrical plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Concept Plants (the breeder's representative), Green Leaf, Brecks, Penn State Trial Gardens, GL Plants, Vertschoor Horticulture, Keep Sake Plants, Rotex flower Bulbs, Hogendoorn, Norseco, W.J. Spaargaren, Express Seed, Zahradnictv Krulikchovi, Stuifbergen, Gloeckner, Helga taimeaed, Baumschule Hortmann, Plantentuin Esveld, olerum, Pasic, and Darwin Plants.

BRIEF DESCRIPTION OF THE DRAWINGS

The accompanying colored photograph illustrates the overall appearance and distinct characteristics of the new *Achillea*. The photographs were taken of a plant 1 year in age as grown outdoors in a 17-cm container in Haarlem, The Netherlands.

The photograph in FIG. 1 provides a side view of the plant of 'Versdidem' in bloom.

Figure 1:
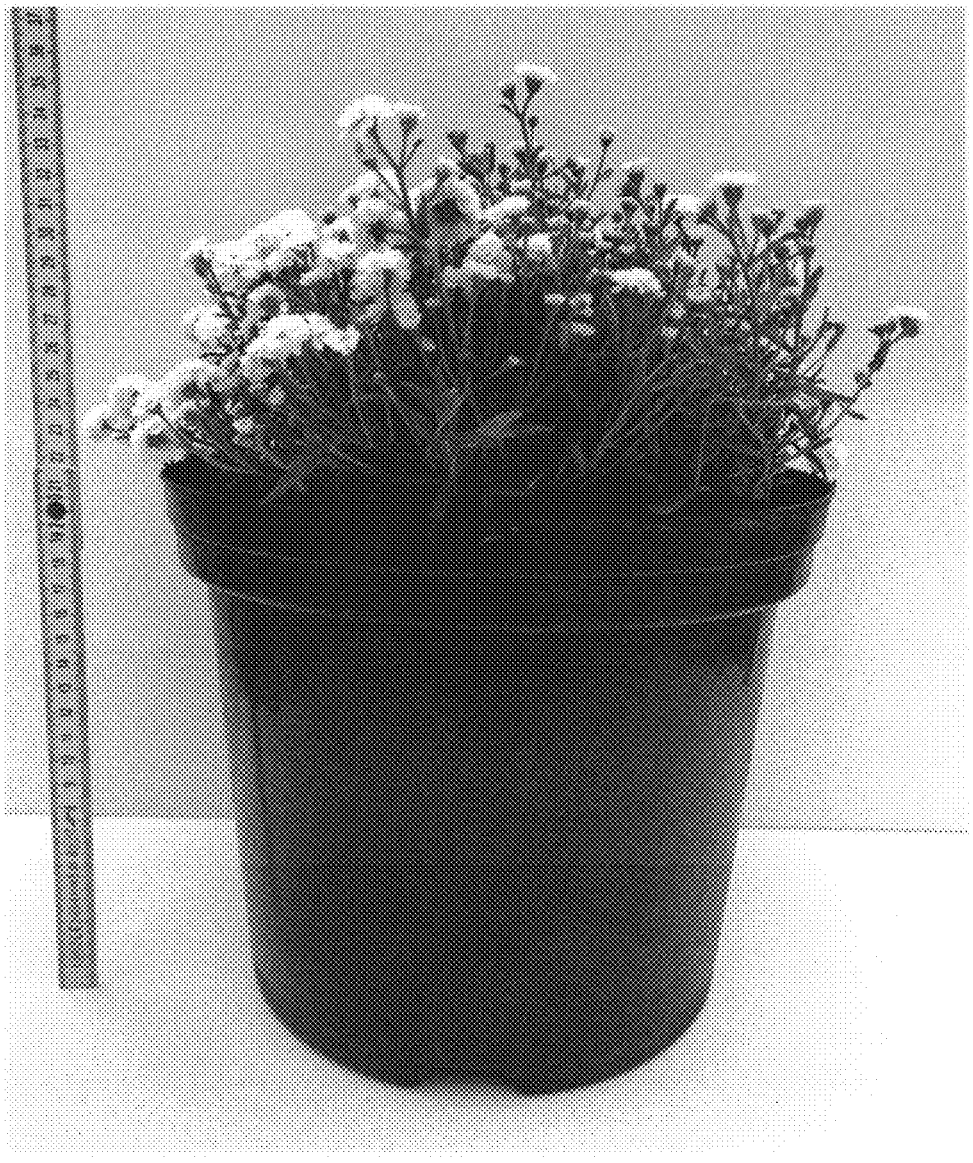
Figure 2:
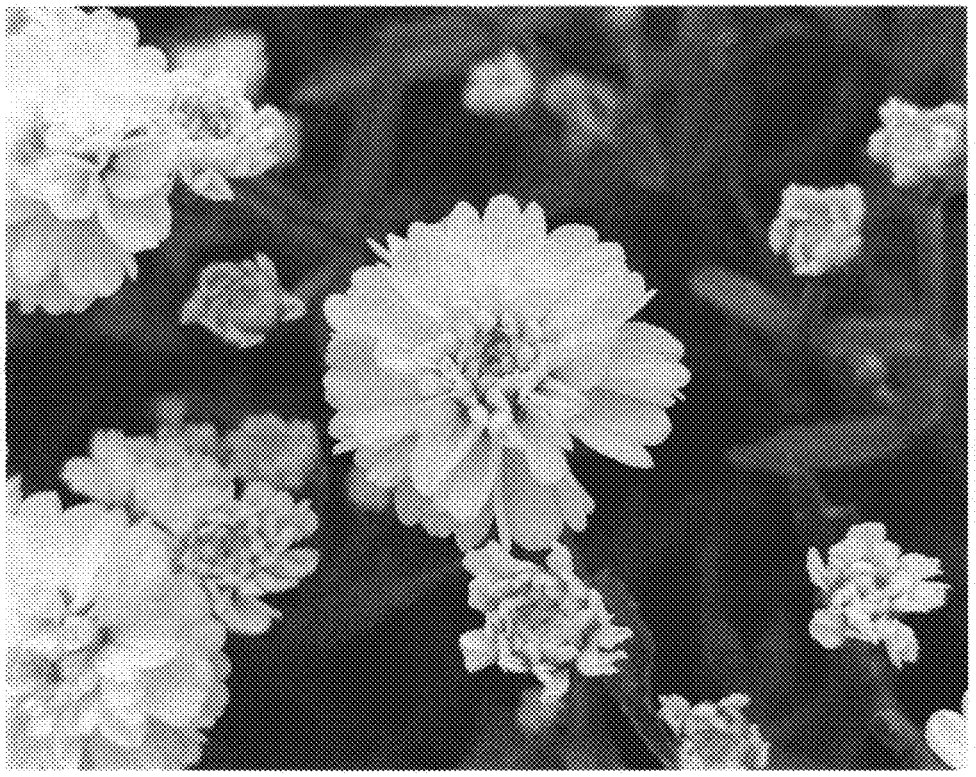

The photograph in FIG. 2 provides a close up of the inflorescences of 'Versdidem'.

Figure 3:
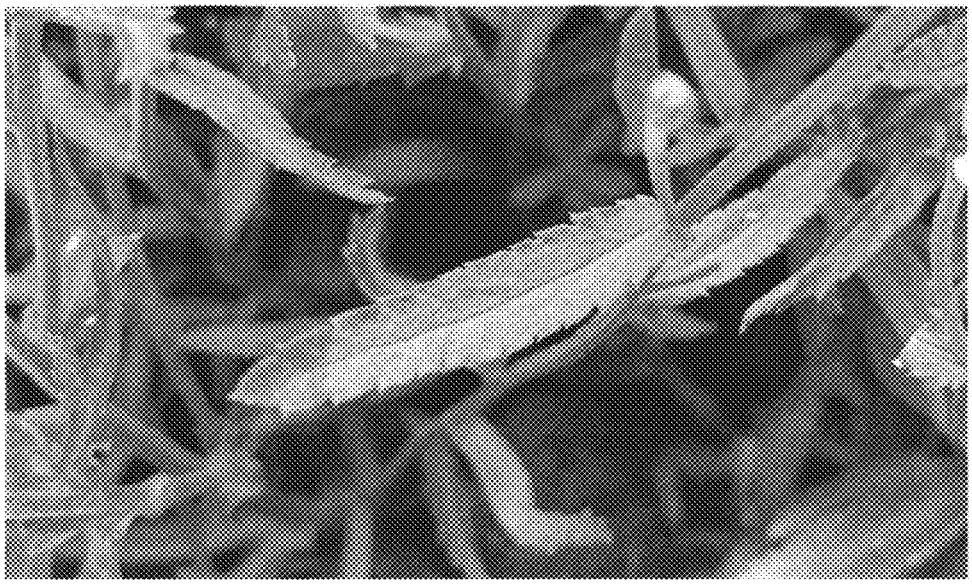

The photograph in FIG. 3 provides a close up view of the foliage of 'Versdidem'.

The colors in the photograph are as close as possible with the digital photography techniques available, the color values cited in the detailed botanical description accurately describe the colors of the new *Achillea*.

DETAILED BOTANICAL DESCRIPTION

The following is a detailed description of 1-year-old plants of the new cultivar as grown outdoors in 17-cm containers in Haarlem, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms July to September and then reblooms after pruning in The Netherlands.

*Plant type*.—Herbaceous perennial.

*Plant habit*.—Compact, rounded and dense.

*Height and spread*.—An average of 16.5 cm in height and 31 cm in width as a one-year-old plant in a container, reaches up to 30 cm in height and 60 cm in spread in the landscape.

*Hardiness*.—At least in U.S.D.A. Zones 3 to 8.

*Diseases and pests*.—Good resistance to powdery mildew has been observed (typically caused by *Podosphaera xanthii*, no susceptibility or resistance to pest has been observed.

*Root description*.—Fibrous.

*Propagation*.—Stem cuttings.

*Root development*.—21 to 24 days for root initiation, 12 weeks to produce a young plant in a 12-cm container.

*Growth rate*.—Highly vigorous.

Stem description:

*Shape*.—Round.

*Stem color*.—145A in color.

*Stem size*.—Up to 15 cm in length and 2.5 mm in diameter.

*Stem surface*.—Pubescent, covered with soft hairs on immature stems, sparse hair on mature stems.

*Branching habit*.—Compact and freely branching.

*Stem number*.—Average of 29 per plant.

*Internode length*.—Up to 2 cm in length.

Foliage description:

*Leaf division*.—Simple.

*Leaf shape*.—Lanceolate to linear.

*Leaf base*.—Attenuate.

*Leaf apex*.—Acute.

*Leaf margin*.—Finely serrate.

*Leaf venation*.—Only midrib is visible, matches leaf color on both surfaces with 144A towards the base.

*Leaf quantity*.—Average of 8 per lateral branch.

*Leaf attachment*.—Sessile.

*Leaf arrangement*.—Alternate.

*Leaf surface*.—Upper surface slightly glossy, lower surface pubescent mostly on the young leaves.

*Leaf color*.—Young and mature upper surface; 137A, young lower surface; 144C, mature lower surface; 137C.

*Leaf size*.—Up to 3.8 cm in length, 7 mm in width.

Flower description:

*Inflorescence type*.—Composite on terminal and upper nodes of stems.

*Inflorescence size*.—Up to 1.2 cm in height, 1.8 cm in width.

*Inflorescence quantity*.—Average of 23 per stem.

*Lastingness of inflorescence*.—About 7 to 10 days until senescence of ray flowers. Bracts and disk flowers are persistent.

*Flower fragrance*.—None.

*Flower buds*.—4 mm in length and diameter, round in shape, 137C in color.

*Peduncle*.—Up to 4 cm in length, 2 mm in diameter, 137C in color, surface is sparsely pubescent.

*Pedicel*.—None.

*Receptacle*.—Not distinct, small, chaffy, 144A in color.

*Involucral bracts*.—None.

Ray florets:

*Number*.—Up to 90.

*Shape*.—Oblong to ovate.

*Size*.—Average of 7 mm in length, 5 mm in width.

*Petal apex*.—Tri-lobed.

*Petal base*.—Fused.

*Petal margins*.—Entire.

*Petal texture*.—Smooth.

*Color*.—Upper and lower surfaces 155D.

Disk flowers:

*Quantity*.—25 to 30.

*Shape*.—Narrow funnel-shaped.

*Size*.—Average of 4 mm in length and up to 1 mm in width.

*Apex*.—Broadly acute.

*Color*.—Base (tube) is 149D in color, apex is 2D.

Reproductive organs:

*Gynoecium*.—(Present on ray florets only), pistil; 1 per floret, up to 3 mm in length, stigma; bifid, 151B in color and translucent, style; average of 4 mm in length, 0.25 mm in diameter, 151B in color and translucent, ovary; not observed.

*Androecium*.—(Present on disc florets only), stamens; one per floret, filament; 2 mm in length, 0.15 mm in diameter and 150D in color, pollen; moderate in quantity, 9A in color.

*Fruit and seed*.—None observed to date.

It is claimed:

1. A new and distinct cultivar of *Achillea* plant named 'Versdidem' as herein illustrated and described.

* * * * *